United States Patent [19]

Barreras

[11] Patent Number: 4,510,945
[45] Date of Patent: Apr. 16, 1985

[54] P WAVE DETECTION SYSTEM

[75] Inventor: Francisco J. Barreras, Miami, Fla.

[73] Assignee: Cordis Corporation, Miami, Fla.

[21] Appl. No.: 397,026

[22] Filed: Jul. 12, 1982

[51] Int. Cl.³ .............................................. A61B 5/04
[52] U.S. Cl. .................................................... 128/696
[58] Field of Search ............................... 128/696–706, 128/419 P, 419 PG

[56] References Cited

U.S. PATENT DOCUMENTS

| | | | |
|---|---|---|---|
| 3,144,019 | 8/1964 | Haber | 128/2.06 |
| 3,606,882 | 9/1971 | Abe et al. | 128/2.06 |
| 3,747,604 | 7/1973 | Berkovits | 128/419 P |
| 3,757,791 | 9/1973 | Berkovits | 128/419 P |
| 3,878,833 | 4/1975 | Arneson et al. | 128/708 X |
| 3,903,897 | 9/1975 | Woollons et al. | 128/419 PG |
| 3,923,941 | 12/1975 | Stasz et al. | 128/2.06 R |
| 3,939,824 | 2/1976 | Arneson et al. | 128/2.05 A |
| 4,091,817 | 5/1978 | Thaler | 128/419 PG |
| 4,181,135 | 1/1980 | Andresen et al. | 128/703 |
| 4,298,007 | 11/1981 | Wright et al. | 128/419 PG |
| 4,342,318 | 8/1982 | Engle et al. | 128/708 |
| 4,393,877 | 7/1983 | Imran et al. | 128/705 |

OTHER PUBLICATIONS

Parsonnet, Myers and Kresh, "Characteristics of Intracardiac Electrograms II: Atrial Endocardial Electrograms", *PACE*, Jul.-Aug. 1980, vol. 3, pp. 406–417.

*Primary Examiner*—Lee S. Cohen
*Assistant Examiner*—Francis J. Jaworski
*Attorney, Agent, or Firm*—Kenway & Jenney

[57] ABSTRACT

A system for detecting P waves samples a cardiac signal during first and second time periods set by a clock signal. Comparators determine whether the signal increases in voltage during the time periods by a predetermined value, testing whether the slew rate of the signal falls within a range corresponding to the slew rate of a P wave. Latches responsive to the comparators provide input to a logic circuit whose output clocks a counter. Three successive positive samples input into the counter will cause the counter to generate a signal indicating a P wave has been detected.

3 Claims, 3 Drawing Figures

4,510,945

P WAVE DETECTION SYSTEM

BACKGROUND OF THE INVENTION

The invention relates generally to the sensing of cardiac signals, and more particularly to a system for readily identifying the P wave portion of the signal.

There are two major pumping chambers in the heart, the left and right ventricles. Simultaneously contracting, these chambers expel blood into the aorta and the pulmonary artery. Blood enters the ventricles from the left and right atria, respectively. The atria are smaller antechambers which contract in a separate action that precedes the major ventricular contraction by an interval of about 100 milliseconds (ms), known as the AV delay, approximately one-eighth of the cardiac cycle. The contractions arise from a wave of electrical excitation which begins in the right atrium and spreads to the left atrium. The excitation then enters the atrio-ventricular (AV) node which delays its passage via the bundle of His into the ventricles.

Electrical signals corresponding to the contractions may be displayed on an electrocardiagram. A small signal known as the P wave accompanies atrial contraction while a much larger signal, known as the QRS complex, with a normally predominant R wave, accompanies the ventricular contraction. Repolarization prior to the next contraction is marked by another small signal in the electrocardiagram known as the T wave. Reliable detection of the P wave is greatly desirable because the P wave is an extremely useful timing signal for devices that artificially stimulate the heart muscle.

For example, one of the problems treated by cardiac pacers is heart block caused by impairment of the ability of the bundle of His to conduct normal excitation from the atrium to the ventricle. It has long been apparent that in treating this form of heart disease, it is desirable to base the stimulation of the ventricles on the unimpaired P wave cycle. This synchronization maintains the heart's normal physiological pacing pattern. Thus, the sino-atrial node, which governs the interval between atrial depolarizations (i.e., the atrial rate) according to the body's needs, controls the artificial ventricular rate in the normal manner.

The functioning of so called physiological pacing systems based on atrial timing depends on the accuracy of intracardiac detection of the natural P wave. AV sequential pacers operating in the double demand (DDI) mode, for example, also depend on P wave discrimination for inhibiting unnecessary and potentially detrimental atrial stimulation.

For these and other reasons, the ready identification of a P wave in intracardiac systems is desirable.

In an article entitled "Characteristics of Intracardiac Electrograms II: Atrial Endocardial Electrograms" by Victor Parsonnet et al., appearing in the journal Pace, Vol. 3, p. 406 (July-August 1980), it has been proposed that the differences between amplitude and slew rates of P and R waves recorded from the atrial appendage should allow sensing amplifiers to easily distinguish them by means of appropriate filter design.

SUMMARY OF THE INVENTION

Accordingly, it is an object of this invention to provide a P wave intracardiac detection system, and particularly one that discriminates against R wave related signals appearing on the atrial lead.

These and other objects of the invention are accomplished by providing a P wave detection system that does not rely on amplitude discrimination or analog filtering but employs sampling means for receiving a cardiac signal and sampling it for periods substantially less than the duration of a P wave, the sampling means including adjustable timing means for determining whether the sampled cardiac signal has a slew rate within a predetermined range of slew rates and means for generating a signal when said sampled cardiac signal is determined to have a slew rate corresponding to the slew rate of a P wave.

In the preferred embodiment, a sample clock generates consecutively alternating first and second sample windows of long and short durations, respectively. The sampled cardiac signal is checked to see whether it has a slew rate great enough so that the voltage increase of the signal exceeds a predetermined voltage level within the first window, and has a slew rate low enough so that the voltage increase of the signal falls short of the same predetermined voltage level within the second window. A first latch means is arranged to be set only if the sampled signal rises above the predetermined voltage level, and a second latch means is arranged to be set only if the sampled signal does not rise above the voltage level during the second duration. A logic circuit connected to the latches produces an output signal indicating that the slew rate criterion is satisfied. The preferred embodiment also includes counting means arranged to receive the output of the logic circuit, for counting a predetermined number of output signals generated in successive sampling cycles to indicate that the sampled cardiac signal has a slew rate corresponding to the slew rate of a P wave. Time varying means may also be included for automatically adjusting the duration of the first and second sample windows.

DESCRIPTION OF THE PREFERRED EMBODIMENT

Figure 1:
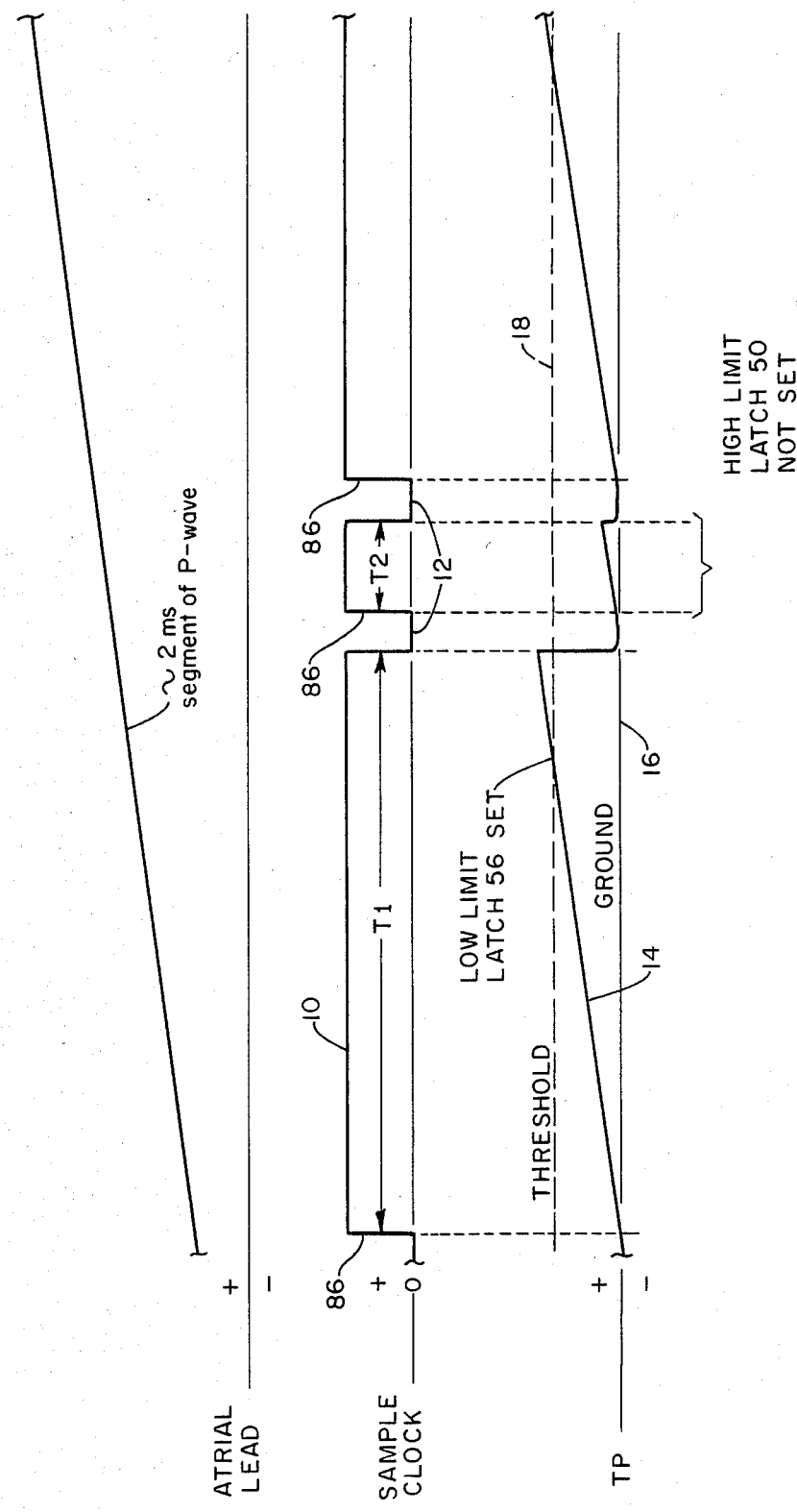
FIG. 1 is a timing diagram of waveforms undergoing the sampling process according to the invention.
Figure 2:
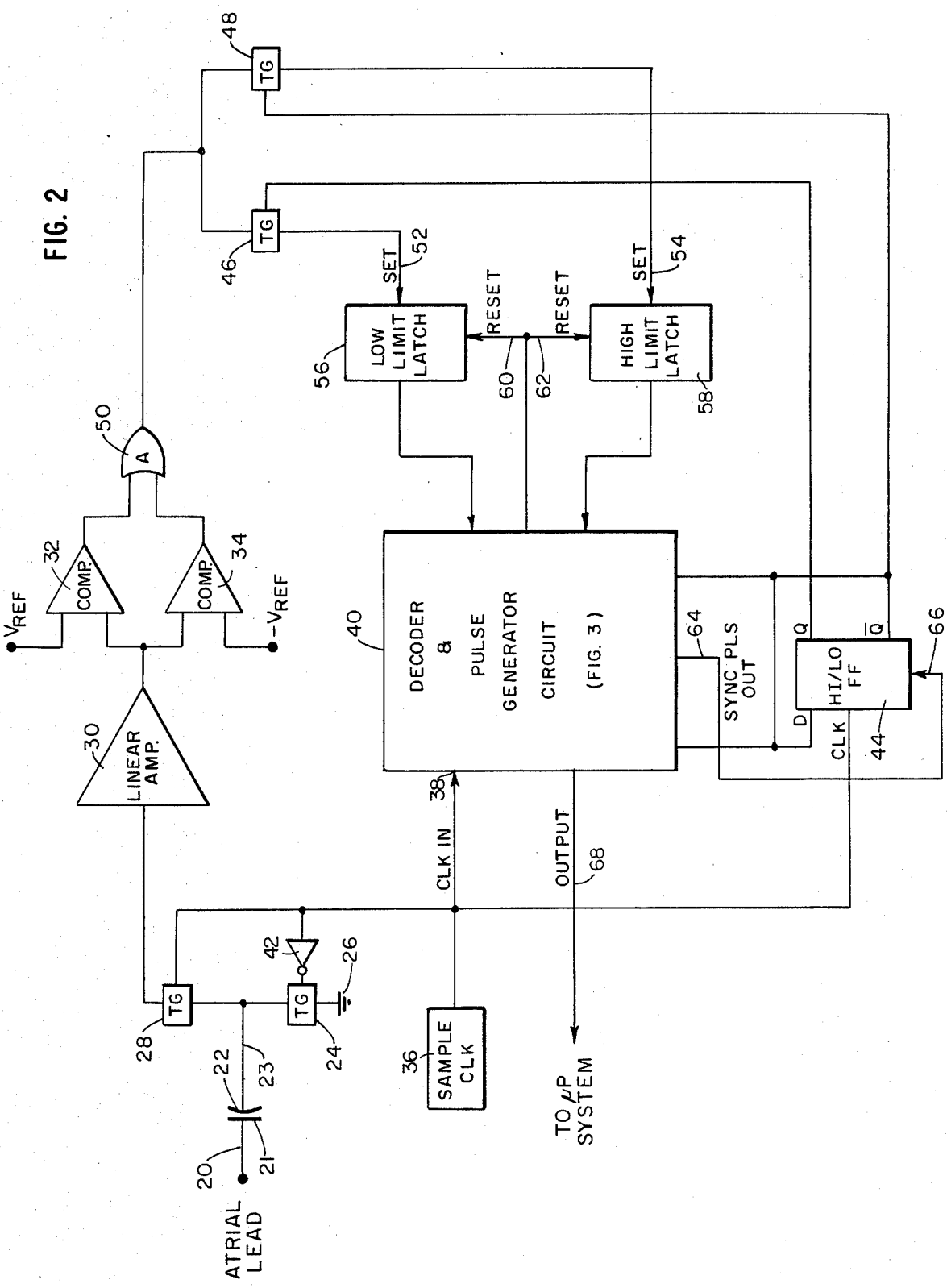
FIG. 2 is a functional block diagram of the P wave detection system according to the invention.
Figure 3:
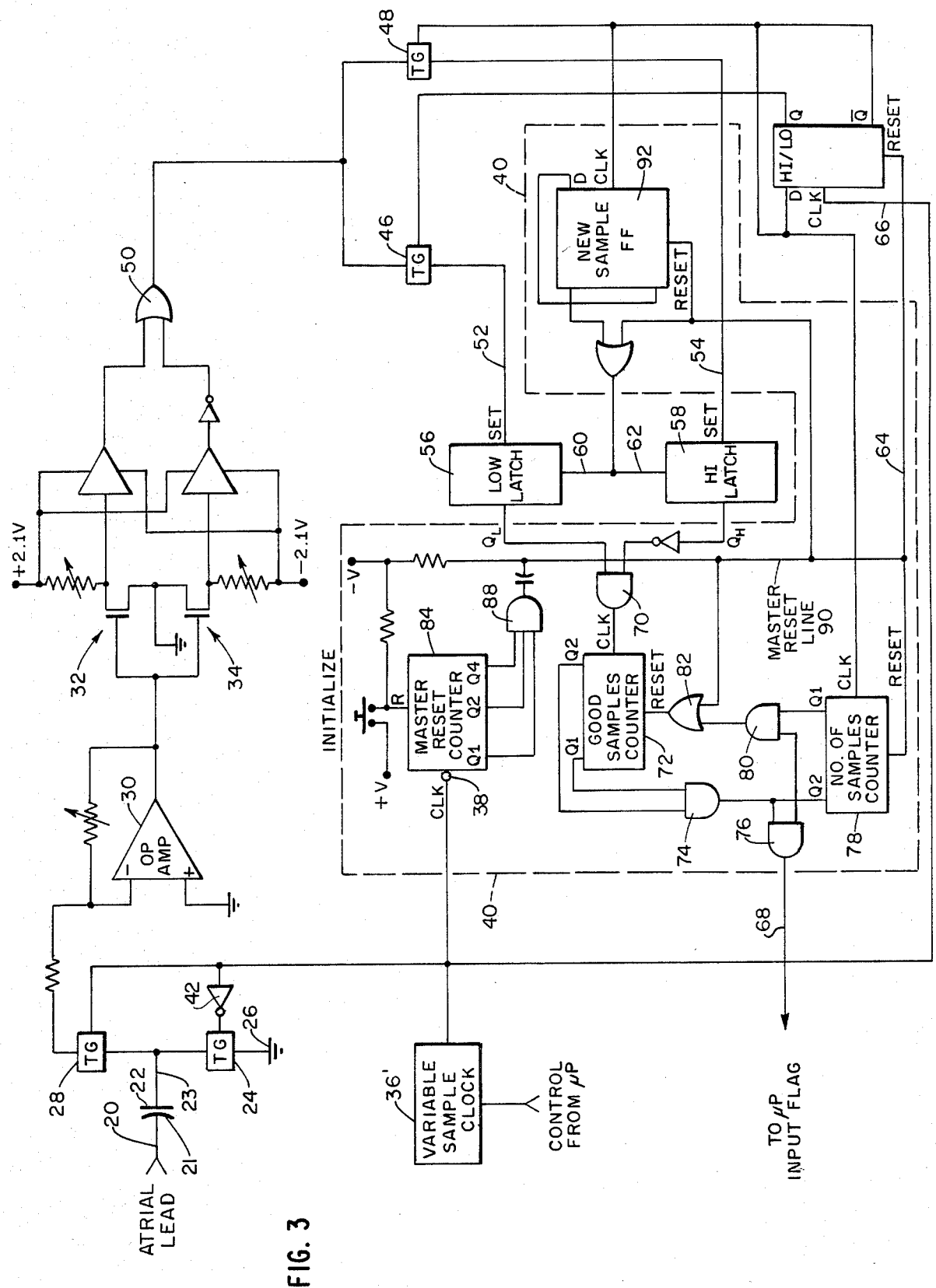
FIG. 3 is an electrical schematic diagram of the P wave detection system of FIG. 2 in more detail.

The system illustrated in FIGS. 1-3 is designed for detection of P waves appearing on a typical pervenous intracardiac atrial lead for use in either cardiac pacing or monitoring. The objective in this embodiment is to discriminate against spurious R waves on the atrial lead in favor of P waves. Because the amplitude of the cross-coupled R wave on the atrial lead is capable of confusing ordinary sense amplifiers, the discrimination strategy is based solely on whether the slew rate of the sampled signal (i.e., the rate of change in amplitude) falls within a prescribed range of slew rates characteristic of the patient's P wave.

A typical intracardiac P wave lasts about 50 milliseconds. The duration of the sampling periods used in the system to be described is on the order of 1 millisecond. As a result, a sufficiently accurate picture of the slew rate of the cardiac signal being sampled may be obtained. Because of the sampling rate there is time to take several samples, count them, and generate a P wave detection signal only if a number of successive acceptable signals from the first stage of detection are received.

As shown in FIG. 1, the duration of the first of the sampling periods T1 is typically one millisecond and that of the second T2, 154 microseconds. During both sampling periods the test is whether the change in voltage of the sampled cardiac signal exceeds 0.5 millivolts. If the sampled cardiac signal change rises above 0.5 millivolts during the first time window of one millisecond, it is above the minimum slew rate determined by that time and voltage (0.5 millivolt/millisecond). If the sampled cardiac signal change fails to rise above 0.5 millivolt during the second time window of 154 microseconds, it is below the maximum slew rate determined by that time and voltage (0.5 millivolt/154 microseconds). The minimum and maximum slew rates are chosen to bracket a range of slew rates characteristic for the patient's P waves.

While the maximum and minimum slew rates against which the cardiac signal is tested can be varied by changing the sampling windows to accommodate different patients, the voltage threshold may remain at 0.5 millivolts. The durations of the sampling windows may be easily varied by a microprocessor. The microprocessor can, for example, determine the maximum slew rate of the P wave of a particular patient by initially setting T2 at a very long duration (i.e. 0.8 milliseconds) and then decrementing the T2 duration with each heartbeat until the threshhold of 0.5 millivolts is not reached within the T2 time interval. Similarly, the microprocessor can determine the minimum slew rate of the same P wave by initially setting T2 to a very short time (i.e. 50 microseconds) and then incrementing T2 with each heartbeat until the threshhold is reached within the T2 time interval.

In the timing diagrams of FIG. 1, the time window line 10 of FIG. 1 illustrates the sample windows. T1 indicates the length of time of the first test period, T2 indicates the length of time of the second period. The long and short time windows alternate. The intervals 12 between the sampling periods indicate where, by discharge of a series input capacitor (22 of FIG. 2), the voltage sample is restored to a zero level. Thus at the beginning of each sampling period the signal (TP, FIG. 2) to be tested starts out from ground and rises at approximately the same rate as the signal on the atrial lead.

FIG. 1 shows a segment 14 of signal TP being tested. The signal TP is one of rising voltage that, during the time, T1, of the first window, rises an amount equal to the difference between ground (or zero) 16 and the threshhold level 18. During the time, T2, of the second window, the signal TP does not rise to the threshhold level. Thus in this instance the slew rate criterion for a bona fide P wave is satisfied.

FIGS. 2 and 3 show a functional block diagram and a corresponding electrical schematic diagram for a circuit that performs the testing function. The electrical components shown in FIGS. 2 and 3 are illustrated using conventional electrical notation.

Referring now to FIG. 2, the intracardiac voltage signal appears on an input lead 20 connected to the atrial lead. The lead 20 presents the cardiac signal to the testing circuit at one side 21 of a capacitor 22. The other side 23 of the capacitor 22 is connected via a first clock-controlled transmission gate 24 to ground 26 and via a second complementary clock-controlled transmission gate 28, through a linear amplifier 30, to parallel positive and negative comparators 32 and 34. A clock signal, generated by a sample clock circuit or microprocessor 36, is presented to the clock signal input 38 of a decoding and pulse generating circuit 40, to the clock-controlled transmission gates 24, 28 (to the first clock-controlled transmission gate 24, via an inverter 42), and to a "HI/LO" flip-flop circuit 44.

The flip-flop circuit 44 controls third and fourth transmission gates 46 and 48 that pass the output of an OR gate 50, whose inputs are the outputs of the comparators 32, 34, to the set inputs 52, 54 of a low limit latch or flip-flop 56 and a high limit latch 58 respectively.

The output of the latches 56, 58 is directed to the decoding and pulse generating circuit 40. The decoding and pulse generating circuit 40 provides a pulse to the reset inputs 60, 62 of the latches 56, 58 at the completion of each sample. The decoding and pulse generating circuit 40 has a synchronizing pulse output 64 connected to the reset input 66 of the flip-flop circuit 44. Finally, the decoding and pulse generating circuit 40 produces an output 68 when three successive samples show all the samples to have had a slew rate between the maximum and minimum slew rates, or the "slew rate window," established by the circuit 40.

FIG. 3 shows greater detail for the circuit of FIG. 2. In particular the logic circuitry of the decoding and pulse generating circuit 40 is illustrated. The output of low latch 56 and complement of the Q output of high latch 58 are fed to AND gate 70 whose output forms the clock input to two-bit ("good samples") counter 72. The parallel outputs of counter 72 are ANDED for "3" in gate 74 and passed to two-input AND gate 76, whose output forms the "good sample" signal. The other input to gate 76 is from the $Q_2$ output of two-bit ("No. of samples") counter 78 clocked by the Q-bar output of HI/LO latch 44. The $Q_1$ and $Q_2$ outputs of counter 78 are ANDED in gate 80 and fed via OR gate 82 to reset the good samples counter 72. Three-bit master reset counter 84 is connected as shown in FIG. 3 to count the sample windows from sample clock 36. The leading (positive-going) edge 86 (FIG. 1) of each sample window forms the clock input to the counter 84. The outputs of counter 84 are ANDED for "7" in gate 88 whose output is capacitively coupled as shown to the master reset line 90 which resets all other counters and latches in the circuit of FIG. 3, as shown. In addition, latches 56 and 58 are simultaneously reset by the Q output of "new sample" flip-flop 92 clocked by the complement of the output of HI/LO flip-flop 44.

In operation, starting from the zero count, a "good" sample sets low latch 56, fails to set high latch 58 and clocks good sample counter 72. Unless the next two samples are "good", counter 72 will not reach "3" since it is reset to zero after three samples by counter 78. After seven samples all of the logic is synchronously reset by master reset line 90.

The system of the invention performs excellent discrimination between P and R waves on the atrial lead, so that synchronous operation of implanted cardiac pacers dependent on detection of P waves will be reliable. However, the slew rate detection system is also applicable to ventricular leads to distinguish between T waves and PVC's, for example.

If a microprocessor is used to control or generate the "sample clock" signal, it can also determine the slew rate of an individual patient's P wave and more precisely set the slew rate limits of the detector circuit accordingly. For example, a tracking slew rate window system may be implemented by scanning the slew range limits stepwise until a predetermined number of good samples are found. After a predetermined interval without any good samples, for example, the slew rate window would begin to scan. In this manner a factory-set P wave detection system can adapt itself not only to different patients but to differing conditions within the same patient. Alternatively, or in addition, the slew rate parameters can be externally programmable.

The advantages of this system also include eliminating the need for setting amplifier sensitivities. A single sense amplifier can be used for both atrial and ventricular channels by multiplexing. The system also enables the possibility of eliminating refractory periods in cardiac pacers by discriminating against T waves and cross-coupled R waves.

Other modifications and adaptations of the circuit of the illustrative embodiment may be made without departing from the spirit of the invention set forth in the following claims.

What is claimed is:

1. A system for detecting the P wave on an intracardiac lead, comprising means for synchronously generating a test signal proportional to the signal on the cardiac lead, thus having approximately the same slew rate as the intracardiac signal, sample timing means for establishing alternately long and short relative sample time windows, means for resetting said test signal to a known level at the beginning of each of said sample windows, means for registering whether the test signal exceeded a predetermined threshold during said sample windows, respectively, and means responsive to said registering means for producing a good sample signal when said test signal exceeded the threshold during the long sample window but did not exceed the threshold during the short sample window, whereby the good sample signal indicates that the corresponding intracardiac signal waveform was within a predetermined range of slew rates characteristic of the patient's P wave.

2. The system of claim 1 further including counting means for producing a detection signal when a predetermined number of good sample signals occur within a predetermined number of cycles to said sample windows.

3. The system of claim 2, further including means for incrementally changing the durations of said sample windows if said detection signal is absent for a predetermined time.

* * * * *